(12) United States Patent
Lamraoui

(10) Patent No.: US 11,872,116 B2
(45) Date of Patent: *Jan. 16, 2024

(54) IMPLANTABLE OCCLUSION SYSTEM

(71) Applicant: UROMEMS, Grenoble (FR)

(72) Inventor: Hamid Lamraoui, Grenoble (FR)

(73) Assignee: UROMEMS, Eybens (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/970,113

(22) Filed: Oct. 20, 2022

(65) Prior Publication Data

US 2023/0044610 A1 Feb. 9, 2023

Related U.S. Application Data

(63) Continuation of application No. 16/836,599, filed on Mar. 31, 2020, now Pat. No. 11,504,219, which is a
(Continued)

(30) Foreign Application Priority Data

Nov. 25, 2014 (FR) ...................................... 1461420

(51) Int. Cl.
*A61F 2/00* (2006.01)
*G16H 10/60* (2018.01)

(52) U.S. Cl.
CPC ...... *A61F 2/004* (2013.01); *A61F 2210/0014* (2013.01); *A61F 2250/001* (2013.01);
(Continued)

(58) Field of Classification Search
CPC .............. A61F 2/004; A61F 2210/0014; A61F 2250/0003; A61F 2250/001; A61F 2250/0013; G16H 10/60
(Continued)

(56) References Cited

U.S. PATENT DOCUMENTS 3,744,063 A 7/1973 Mcwhorter
4,222,377 A 9/1980 Burton
(Continued)

FOREIGN PATENT DOCUMENTS

AU 2002352060 A1 6/2003
CA 1248303 A 1/1989
(Continued)

OTHER PUBLICATIONS

Super-precision double direction angular contact thrust ball bearings. pp. 1-28, SKF, 2012.
(Continued)

*Primary Examiner* — Sunita Reddy
(74) *Attorney, Agent, or Firm* — Thomas | Horstemeyer, LLP

(57) ABSTRACT

An occlusion system implantable in a human or animal body, including a fluidic circuit which includes an inflatable occlusive sleeve, a reservoir with variable volume filled with a fluid. The reservoir includes a fixed portion and a movable portion, an actuator mechanically coupled with the movable portion of the reservoir to linearly displace the movable portion relative to the fixed portion for adjusting the volume of the reservoir. The actuator and the reservoir are laid out in a sealed casing containing a gas. A sensor mechanically bound to the actuator and/or to the movable portion, measures a traction and/or compressive force of the movable portion of the reservoir. Also included is a device for measuring the fluid pressure in the fluidic circuit.

8 Claims, 4 Drawing Sheets

Related U.S. Application Data continuation of application No. 16/426,537, filed on May 30, 2019, now Pat. No. 11,058,527, which is a continuation of application No. 15/529,413, filed as application No. PCT/EP2015/077586 on Nov. 25, 2015, now Pat. No. 10,350,044.

(52) U.S. Cl.
CPC .............. *A61F 2250/0003* (2013.01); *A61F 2250/0013* (2013.01); *G16H 10/60* (2018.01)

(58) Field of Classification Search
USPC ............................. 600/29–31; 128/897, 899
See application file for complete search history.

(56) References Cited

U.S. PATENT DOCUMENTS

| | | | |
|---|---|---|---|
| 4,408,597 A | 10/1983 | Tenney, Jr. | |
| 4,581,018 A | 4/1986 | Jassawalla | |
| 4,634,443 A | 1/1987 | Haber | |
| 4,994,019 A | 2/1991 | Fernandez | |
| 6,135,945 A | 10/2000 | Sultan | |
| 6,482,145 B1 | 11/2002 | Forsell | |
| 7,217,237 B2 | 5/2007 | Wassermann | |
| 8,348,826 B2 | 1/2013 | Gomez-Llorens | |
| 8,585,580 B2 | 11/2013 | Vaingast | |
| 9,814,561 B2 | 11/2017 | Forsell | |
| 2003/0045775 A1* | 3/2003 | Forsell | A61F 2/0018 600/31 |
| 2005/0240144 A1 | 10/2005 | Wassemann | |
| 2005/0267500 A1* | 12/2005 | Hassler, Jr. | A61F 5/0003 606/157 |
| 2007/0232848 A1 | 10/2007 | Forsell | |
| 2008/0177398 A1 | 7/2008 | Gross | |
| 2008/0249806 A1* | 10/2008 | Dlugos | A61B 5/4205 607/60 |
| 2009/0056750 A1 | 3/2009 | Ott | |
| 2010/0211175 A1 | 8/2010 | Gomez-Llorens | |
| 2011/0087337 A1 | 4/2011 | Forsell | |
| 2011/0124955 A1 | 5/2011 | Ciquin | |
| 2012/0157759 A1* | 6/2012 | Wirbisky | A61F 2/004 600/31 |
| 2012/0184980 A1 | 7/2012 | Anderson | |
| 2013/0274546 A1 | 10/2013 | Anderson | |
| 2015/0223923 A1 | 8/2015 | Forsell | |
| 2015/0374288 A1 | 12/2015 | Lamraoui | |
| 2016/0089224 A1* | 3/2016 | Taylor | A61F 2/004 600/30 |
| 2016/0106527 A1* | 4/2016 | Taylor | A61F 2/004 600/31 |
| 2018/0243074 A1 | 8/2018 | Forsell | |

FOREIGN PATENT DOCUMENTS

| | | |
|---|---|---|
| EP | 1584303 A1 | 10/2005 |
| JP | 2009540964 A5 | 8/2010 |
| WO | 2007149992 A1 | 12/2007 |
| WO | 2009056750 A2 | 5/2009 |
| WO | 2014118335 A1 | 8/2014 |

OTHER PUBLICATIONS

International Preliminary Report on Patentability received for PCT Patent Application No. PCT/EP2015/077586, dated Jun. 8, 2017, 13 pages (7 pages of English Translation and 6 pages of Original Document).

Office Action received for European Patent Application No. 15800824. 3, dated Mar. 2, 2018 5 pages of Original Document only.

Lamraoui, H., et al., "Development of a Novel Artificial Urinary Sphincter: A Versatile Automated Device," IEEE/ASME Transactions on Mechatronics, vol. 15, No. 6, Dec. 201 O.

Uromems, "French Preliminary Search Report," FR Application No. 1461420 (dated Apr. 28, 2015) (with English translation cover sheet).

Uromems, "International Search Report and Written Opinion," PCT Application No. PCT/EP2015/077586 (dated Feb. 15, 2016) (with English translation cover sheet).

* cited by examiner

IMPLANTABLE OCCLUSION SYSTEM

CROSS-REFERENCE TO RELATED APPLICATION APPLICATIONS

This application is a Continuation Application of U.S. application Ser. No. 16/836,599, filed Mar. 31, 2020 entitled "Implantable Occlusion System", which application is a Continuation Application of U.S. application Ser. No. 16/426,537, filed May 30, 2019, now U.S. Pat. No. 11,058,527 entitled "Implantable Occlusion System", which application is a Continuation Application of U.S. application Ser. No. 15/529,413, filed May 24, 2017, now U.S. Pat. No. 10,350,044, entitled "Implantable Occlusion System", which application is a 371 International Application, PCT No. PCT/EP2015/077586, filed Nov. 25, 2015 entitled "Implantable Occlusion System", which claims priority to French Application No. 1461420, filed Nov. 25, 2014, the contents of which being incorporated by reference in their entirety entireties herein.

FIELD OF THE INVENTION

The present invention relates to an implantable occlusion system in a human or animal body.

BACKGROUND OF THE INVENTION

It is known how to occlude an anatomic conduit by means of an occlusion system implantable into the body of a patient.

The occlusion of the anatomic conduit is ensured by an inflatable sleeve filled with fluid which exerts a more or less strong pressure on the portion to be occluded depending on the volume of the fluid in the inflatable sleeve.

For example, various urinary artificial sphincters are based on this principle for exerting pressure on the urethra. Among known products, mention may be made of the implant referenced as AMS800 marketed by American Medical Systems or else the implant referenced as ZSI375 marketed by Zephyr. The same principle is found in other types of applications such as gastric rings which include an inflatable sleeve placed around the stomach.

The swellable sleeve filled with fluid may be made in different forms, for example totally or partly surrounding the conduit to be occluded and may be formed with different biocompatible materials, such as implantable silicone, implantable polyurethane, etc.

The injection and the suction of fluid in the inflatable sleeve required for the occlusion of the anatomic portion may be either achieved manually and passively such as for artificial urinary sphincters AMS800 and ZS1375, or automatically and actively (from an electric power source for example) for more developed implants.

In order to allow regulation of the pressure exerted on the conduit to be occluded, the inflatable sleeve is in fluidic connection with a reservoir of fluid coupled with a configured actuator for injecting fluid from the reservoir to the sleeve (in order to increase the pressure exerted on the anatomic conduit) or from the sleeve to the reservoir (for reducing the pressure exerted on the anatomic conduit). The whole of the inflatable sleeve, of the reservoir and of the fluidic connection between them forms a fluidic circuit.

In such an occlusion system, it may be necessary to measure the pressure in the inflatable sleeve or in another point of the fluidic circuit, for example in order to check pressure when the actuator is disabled, or further for controlling the pressure generated by said actuator.

Document EP 1 584 303 thus discloses the use of a pressure sensor implanted on the occlusive sleeve. However such a solution cannot be achieved industrially since it poses problems of integration, bulkiness, seal and biocompatibility of the sensor.

For this purpose, there exist different types of pressure sensors.

Among the sensors which may be contemplated in an implantable system, pressure sensors based on a flexible membrane in contact with the fluid may be used. These sensors nevertheless have to be biocompatible, stable over time, and it is necessary to ensure a perfect seal of the sensor in order to avoid infiltration of fluid or of humidity into the sensor or the associated electronics.

A solution to this problem may be the use of a pressure sensor comprising a flexible metal membrane ensuring the seal of the system. However, such a sensor has several drawbacks. On the one hand, as the metal membrane of the sensor is thin, the manufacturing methods may be delicate. Indeed, the mechanical stresses due to thermal effects of the weld on the membrane may have an effect on the stiffness of the membrane which may induce significant disparities in the mechanical properties of the membrane. Moreover, this type of sensor is generally sealed and filled with a non—compressible fluid in contact with a pressure sensor strictly speaking. The method for assembling the different portions of the system (consisting of several tens of elements) is therefore delicate and costly. Finally, when the system is implanted, the fibrosis surrounding the different elements of the implant may induce a change in stiffness of the membrane and therefore a drift in the measurements over time.

Another problem to be solved is to be able to apply a defined and specific pressure on the anatomic conduit by consuming a minimum of energy.

A simple solution would be to use a system based on the measured occlusion pressure. Among the means for measuring the occlusion pressure, mention may be made of systems which directly measure the pressure in the fluidic circuit via a suitable sensor, or else which measure the pressure indirectly for example from the current consumed by the actuator as described in document U.S. Pat. No. 8,585,580.

However, it has been demonstrated by tests in vivo [1] that the pressure in the fluidic circuit strongly and permanently varies during the occlusion. In the case of a system based on a pressure regulation, this has the effect of quasi—permanently urging the actuator for stabilizing the pressure at a given set value, with the consequence of inducing excessive electric consumption of the system.

Other principles have been proposed, for example document U.S. Pat. No. 8,585,580 proposes a system which transfers a fluid to the inflatable sleeve until the measured pressure exceeds a defined threshold. This solution has the drawback of not being very accurate on the applied occlusion pressure. Indeed, during the occlusion phase, the pressure may strongly increase and then decrease due to the relaxation of the tissues and of the occlusion device. The fluid provided to the occlusion device in contact with the anatomic conduit to be occluded is therefore generally not sufficient for generating the desired pressure.

Moreover, the bulkiness of such a sensor also poses a problem, insofar that the implantable system has to be of dimensions as reduced as possible and that said system further comprises a fluid transfer device, the volume of which has to be consequent and a battery which also represents a large portion of the volume of the implantable system. The integration of such a sensor into this system may be difficult due to the bulkiness of said sensor. Further, as this type of sensor has to be both in contact with the outside, and for the pressure measurement, and with the inside for communicating with the electronic module, it is necessary to apply a reliable and hermetic manufacturing process, such as laser welding, which may be a constraint in a production phase.

Short Description of the Invention

An object of the invention is to design an implantable occlusion system which gives the possibility of getting rid of the drawbacks of the existing systems. In particular, this system should allow measurement of the pressure in the sleeve reliably while being biocompatible, sealed and minimizing the bulkiness of the implantable system and the consumption of energy required for regulating this pressure. Preferably said system should also allow control of the pressure in the sleeve.

For this purpose, an occlusion system is proposed, which is implantable in a human or animal body, comprising:
a fluidic circuit comprising:
 an inflatable occlusive sleeve containing a variable volume of a fluid, intended to surround at least one portion of the natural conduit to be occluded,
 a reservoir with variable volume filled with a fluid, said reservoir comprising a fixed portion and a movable portion,
 a fluidic connection between the reservoir and the occlusive sleeve,
an actuator mechanically coupled with the movable portion of the reservoir so as to linearly displace said movable portion relatively to the fixed portion for adjusting the volume of the reservoir,
the actuator and the reservoir with variable volume being laid out in a sealed casing containing a gas.

According to the invention, said system further comprises:
a sensor laid out in the casing, mechanically connected to the actuator and/or to the movable portion of the reservoir, laid out so as to measure a traction and/or compression force in the direction of displacement of the movable portion of the reservoir, said measured force resulting at least from:
 the force noted as $F_{occl}$ exerted on the movable portion of the reservoir with a variable volume related to the pressure in the fluidic circuit, and
 the force noted as $F_{casing}$ exerted on the movable portion of the reservoir with variable volume related to the pressure in the casing,
a device for measuring the fluid pressure in the fluidic circuit comprising a processing unit configured for determining said fluid pressure from a calculation taking into account at least the force measured by said sensor, the effective pressure surface of the movable portion of the reservoir, and the force $F_{casing}$ exerted on the movable portion of the reservoir with a variable volume related to the gas pressure in the casing.

This system has the following advantages. On the one hand, the fact that the sensor is laid out in the casing, allows measurement of the pressure without any remote element (outside the casing) and therefore avoids application of complex connections leaving the casing and the seal of which has to be ensured. Further, biocompatibility is ensured by the casing and therefore does not generate any specific constraint in terms of the design of the sensor. Finally, as the sensor is integrated to the pressurization system of the sleeve, the required bulkiness is minimized.

According to a preferred embodiment, the system further comprises a device for controlling the fluid pressure in the fluidic circuit by the volume of the reservoir, comprising:
a memory in which is recorded a relationship between the pressure in the fluidic circuit and the volume of said reservoir,
a processing unit configured for:
 receiving a fluid pressure set value in the fluidic circuit,
 from the relationship recorded in the memory between the pressure in the reservoir and the volume of the reservoir, determining the volume of the reservoir with which it is possible to attain the pressure set value,
 if necessary, controlling the actuator for displacing the movable portion of the reservoir into a position defining said determined volume,
a calibration unit configured for:
 (a) when the patient is in a determined situation, controlling the actuator for displacing the movable portion of the reservoir into a plurality of determined positions, each position defining a determined volume of the reservoir,
 (b) for each of said positions:
  measuring the fluid pressure in the fluidic circuit by said device for measuring the fluid pressure in the fluidic circuit,
  updating the memory by recording said fluid pressure measured in the fluidic circuit for the respective volume of the reservoir.

According to an embodiment, the sensor is able to measure traction forces and the compressive forces in the direction of displacement of the movable portion of the reservoir.

According to another embodiment, the sensor is able to exclusively measure compressive forces in the direction of displacement of the movable portion of the reservoir; in this case, the system further comprises a pre—stress device laid out so as to exert a determined compressive pre—stress on said sensor.

In this case, the processing unit is configured for taking into account said pre—stress for determining the fluid pressure in the fluidic circuit.

The pre—stress device advantageously comprises at least one compressive spring, a traction spring and/or an elastomeric pad.

According to an embodiment, the movable portion of the reservoir with a variable volume comprises a driving system coupled with a movable wall and deformable bellows extending and being compressed according to the position of said movable wall.

In this case, the processing unit is advantageously configured so as to take into account the stiffness of said bellows for determining the fluid pressure in the fluidic circuit.

In an advantageous embodiment, the drive system comprises a screw secured to the movable wall and a nut coupled with the screw and rotatably movable on a dual-effect bead abutment around the axis of the screw under the effect of a driving action by the actuator, the nut being coupled with the screw so that rotation of the nut only drives the screw into translation in the displacement direction of the movable portion; moreover, the sensor is laid out in said bead abutment so as to measure at least one traction force and one compression force in the displacement direction of the movable portion of the reservoir.

According to another embodiment, the movable portion of the reservoir with a variable volume comprises a driving system coupled with a rolling membrane.

According to another embodiment, the reservoir with a, variable volume comprises a cylinder forming the fixed portion of the reservoir and a piston sliding in said cylinder, forming the movable portion of the reservoir.

Advantageously, the actuator is selected from piezoelectric actuators, electromagnetic actuators, electro—active polymers and shape memory alloys.

According to an embodiment of the invention, the system further comprises a gas pressure sensor laid out in the casing for measuring the gas pressure in the casing, the processing unit being configured for taking into account said gas pressure measured in the determination of the force $F_{casing}$.

Advantageously, a wall of the reservoir with a variable volume is formed by a wall of the casing, said wall comprising a perforable puncture port.

Advantageously, the system further comprises a device for reducing stresses in the fluidic circuit when said stresses exceed a determined threshold.

According to a preferred embodiment, the system further comprises an accelerometer, the processing unit being configured for determining from measurement data of the accelerometer, whether the patient is in a determined situation.

More advantageously, the device for measuring the pressure is configured for measuring the fluid pressure upon adjusting the volume of the reservoir and for checking the match between said measured value and an expected value.

According to a preferred embodiment of the invention, the system is an artificial urinary sphincter.

According to an embodiment, the treatment unit is configured for calculating a relative fluid pressure in the fluidic circuit, said relative pressure being equal to the difference between the fluid pressure determined in the fluidic circuit and the atmospheric pressure exerted on the patient.

According to an embodiment, the system further comprises a device intended to be placed outside the body of the patient and comprising a barometric sensor suitable for measuring the atmospheric pressure exerted on the patient, said device being able to communicate said pressure measurement to the treatment unit for calculating said relative fluid pressure in the fluidic circuit.

Alternatively, the treatment unit is configured for determining the atmospheric pressure exerted on the patient from the pressure in the fluid circuit and from a known relative pressure of the fluid in the fluidic circuit in a given actuation configuration of the sleeve.

SHORT DESCRIPTION OF THE DRAWINGS

Other features and advantages of the invention will become apparent from the detailed description which follows, with reference to the appended drawings wherein:

FIG. 1 is an overall view of the implantable occlusion system,

FIG. 2 is a sectional view of the inside of the casing of an implantable occlusion system according to a first embodiment of the invention, FIG. 3 is a sectional view of the casing of an implantable occlusion system according to a second embodiment of the invention, FIG. 4 is a sectional view of the casing of an implantable occlusion system according to a third embodiment of the invention, FIG. 5 is a sectional view of the inside of the casing of an implantable occlusion system according to a fourth embodiment of the invention, FIG. 6 is a diagram showing the different forces which may be measured by the compressive or traction force sensor, in the presence of a pre—stress, FIG. 7 is a diagram showing the various forces which may be measured by the compressive and traction force sensor in the absence of any pre—stress, FIG. 8 is a graph showing the variation of the pressure in the fluidic circuit depending on the volume injected into the occlusive sleeve, FIG. 9 is a graph showing the variation of the pressure in the fluidic circuit versus time for different volumes of fluid injected into the occlusive sleeve during the calibration procedure.

DETAILED DESCRIPTION OF EMBODIMENTS OF THE INVENTION

General Presentation of the Implantable Occlusion System

Figure 1:
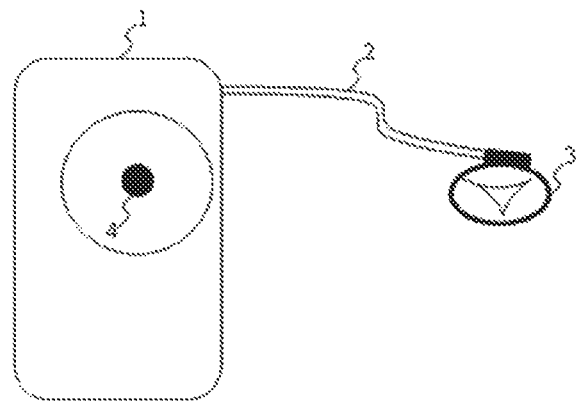

With reference to FIG. 1, the occlusion system comprises an inflatable occlusive sleeve 3 containing a variable volume of a fluid, intended to surround at least one portion of a natural conduit (not shown) to be occluded, and a reservoir 5 with a variable volume (illustrated in FIGS. 2 to 5) filled with a fluid.

The occlusive sleeve may be made of a biocompatible elastomer (cf. for example documents U.S. Pat. No. 4,222, 377, CA 1,248,303 or U.S. Pat. No. 4,408,597).

Said reservoir comprises a fixed portion and a movable portion, the displacement of the movable portion varying the volume of the reservoir.

For this purpose, the occlusion system comprises an actuator mechanically coupled with the movable portion of the reservoir so as to linearly displace said movable portion relatively to the fixed portion in order to adjust the volume of the reservoir. The actuator may notably comprise an electromagnetic motor and a reducer. The actuator is controlled by a device for controlling the pressure of the sleeve which will be described in detail later on.

For each volume of the reservoir, the movable portion has a known effective pressure surface area, which may be constant or variable according to the embodiments.

The occlusion system further comprises a fluidic connection 2 (typically tubing) between the reservoir 5 and the occlusive sleeve 3.

Thus, a variation in volume of the reservoir 5 causes addition or withdrawal of fluid in the sleeve 3, thereby increasing or decreasing the compression exerted on the conduit surrounded by the sleeve.

The assembly formed with the reservoir of variable volume, of the occlusive sleeve and of the fluidic connection is called a fluidic circuit in the following of the description.

In addition to the device for controlling the pressure of the occlusive sleeve, the implantable system includes one or several electronic modules giving the possibility of producing all the required functions. It further includes a rechargeable power source or not, allowing the system to be powered. In a particular configuration, the power source is outside the human body and transmits the energy in a wireless way to the implantable system.

The reservoir with variable volume, the actuator as well as said electronic module(s) and, if necessary, the power source, are laid out in a casing 1 intended to be implanted into the body of the patient. The casing 1 contains a gas, for example air, said casing has to be sealed so as to avoid any transfer of fluid or gas from or to the intracorporeal medium. The casing is in a biocompatible material, and may for example be made in implantable titanium and sealed by laser welding. A check of the seal may notably be achieved with helium (for example, a leak rate of less than $10^{-9}$ mbar.L/s of helium) for ensuring the total seal of the casing during the period for which the device is implanted.

According to a particular embodiment, the casing may contain a gas pressure sensor, the function of which will be described below.

Advantageously, the casing 1 comprises, in a wall delimiting the reservoir with a variable volume, a puncture port 4 which may be perforated with a needle and able to sealably close after withdrawing the needle, allowing injection or withdrawal of the fluid of the reservoir.

The casing also contains a sensor in a mechanical connection with the actuator and/or the movable wall of the reservoir with a variable volume which may measure a compressive and/or traction force in the direction of displacement of the movable portion of the reservoir.

Among the sensors suitable for this use, mention may for example be made of:
- a sensor based on one or several strain gauges (such gauges allow measurement of traction and compressive forces);
- one or several sensors of the FSR™ type (acronym "Force Sensing Resistor") marketed by Interlink Electronics, measuring compressive forces); and/or
- one or several pressure sensors coupled with a mechanism allowing measurement of a force. For example, mention may be made of a hydraulic pressure sensor combined with a pocket full of fluid and laid out so as to measure a pressure on a predetermined surface, thereby allowing inference of the force applied to the measurement surface.

The system may further comprise a device allowing measurement of the atmospheric pressure in the surroundings of the patient. A barometric sensor capable of measuring the current atmospheric pressure exerted on the body of the patient, may for example be laid out in an external device borne by the patient. This measurement may be transmitted by a wireless link to the control device laid out in the implantable casing.

Reservoir with a Variable Volume

According to a preferred embodiment, the reservoir with a variable volume comprises bellows assembled in the casing, the bellows and the casing for example being made in implantable titanium. The reservoir with variable volume then consists of the bellows (acting as a movable portion), of a wall of the casing and of a hood acting with said wall of the casing, as a fixed portion. The reservoir further comprises an orifice allowing transfer of the fluid from and to the outside of the reservoir.

The use of metal bellows for producing the function of a reservoir with variable volume is known to the person skilled in the art (cf. document U.S. Pat. No. 4,581,018 for example). Such bellows are for example marketed by Servometer and Witzenmann.

The bellows have the advantage of ensuring total seal of the implant while allowing movement of the movable wall. Its effective pressure surface area may be considered as constant over the whole range of travel of the bellows.

Nevertheless, it should be taken into account in the design of the device, the mechanical stiffness of the bellows which may have an influence on the behavior of the device (impact on the power yield, direction of the forces, etc.). How this parameter is taken into account will be described in detail below.

However, the present invention is not limited to the use of bellows for forming the reservoir with variable volume. Thus, the person skilled in the art may apply for producing the reservoir with a variable volume, a piston or a rolling membrane, which are considered as not having any mechanical stiffness. In this case, unlike the case of bellows, the stiffness will be considered as zero or negligible in the calculation of the pressure.

The movable portion of the reservoir has an effective pressure surface area which may be constant or variable according to the embodiment of the reservoir.

In the case of bellows, the effective pressure surface area is considered as constant and is given by the manufacturer. For a rolling membrane, the effective pressure surface area varies according to the position of the rolling membrane and is given by the manufacturer for different travel values, In the case of a piston sliding without any friction in a cylinder, the effective pressure surface area is equal to the front surface area of the piston.

Actuator

The actuator may be selected from any electromechanical system allowing transformation of electric energy into a mechanical movement with the required power for allowing the displacement at a force and at a required speed of the movable portion of the reservoir with variable volume. For example mention may be made from among the actuators known to the person skilled in the art, of piezo—electric actuators, of electromagnetic motors with or without brushes (in the case of a brushless motor, the latter may consist of 2 poles or of 4 poles) either coupled or not with a reducer, electro—active polymers or else shape memory alloys.

Figure 2:
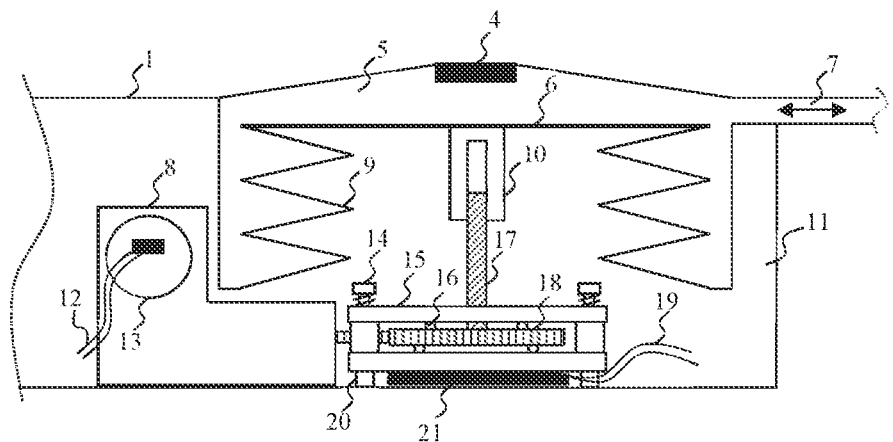

FIG. 2 illustrates an embodiment of the invention and represents a sectional view of a portion of the inside of the casing 1.

The reservoir with variable volume 5 comprises a movable portion which, in this embodiment is bellows 9.

The bellows have a flange 6 coupled with a driving screw 17 via a spotted wheel 10 secured to the flange 6 and having tapping cooperation with the threading of the screw 17.

The reservoir is delimited by a portion of the wall of the casing 1 and of the bellows 9.

The wall of the casing 1 moreover comprises a puncture port 4 which may be perforated by a needle in order to add or withdraw fluid from the reservoir.

The reservoir 5 further comprises a connection 7 for tubing ensuring the fluidic connection with the occlusive sleeve (not shown).

The casing 1 further contains an actuator comprising a motor 13 coupled with a reducer 8. A connector 12 allows the motor 13 to be powered when the control device transmits an order for operating the motor in one direction or in the other depending on whether an increase or a decrease in the volume of the reservoir is required.

The reducer is coupled with a toothed wheel 18 which is itself coupled with the driving screw 17, so as to transmit the torque and the rotation of the axis of the motor 13 to the driving screw 17. Rotation of the screw 17 then drives the spotted wheel 10 into translation, which has the effect of displacing the flange 6 in translation in a direction parallel to the axis of the screw 17, the displacement direction of the flange 6 depending on the direction of rotation of the motor 13.

The inner space 11 of the casing surrounding the reservoir 5 is filled with a gas.

The volume variation of the reservoir 5 therefore has the effect of varying the inner volume 11 and therefore the pressure of the gas in said volume 11.

A gas pressure sensor (not shown) may optionally be laid out in the volume 11 for measuring the pressure in this volume.

The toothed wheel 18 is housed in a block 15 via ball bearings 16 which allow its rotation in the block 15. As the toothed wheel 18 is secured to the driving screw 17, the block 15 is driven into translation in the casing by the screw 17. Pads 20 extend from the wall of the casing 1 parallel to the axis of rotation of the screw 17 allowing guidance of the translation of the block 15.

A force sensor is attached on the wall of the casing facing the face of the block 15 opposite to the reservoir 5. The mark 19 refers to a connector allowing transmission of the measurement data of the sensor to the device for measuring and controlling the pressure.

In this embodiment, the force sensor 21 only measures compressive forces.

In order to nevertheless allow measurement of the traction forces, the system comprises a pre—stress device 14 which exerts a determined compressive force on the force sensor. This pre—stress device thus generates an "offset" on the force sensor, which allows measurement of both the traction forces and the compressive forces.

Said pre—stress device may comprise one or several adjustment screws cooperating with the guiding pads 20 and, interposed between the head of a respective adjustment screw and the block 15, a compressive spring, an extension spring and/or an elastomeric pad.

As this is seen, the integration of the force sensor to the pressurization system of the sleeve is particularly compact and is therefore not a penalty for the bulkiness of the implantable system.

Figure 3:
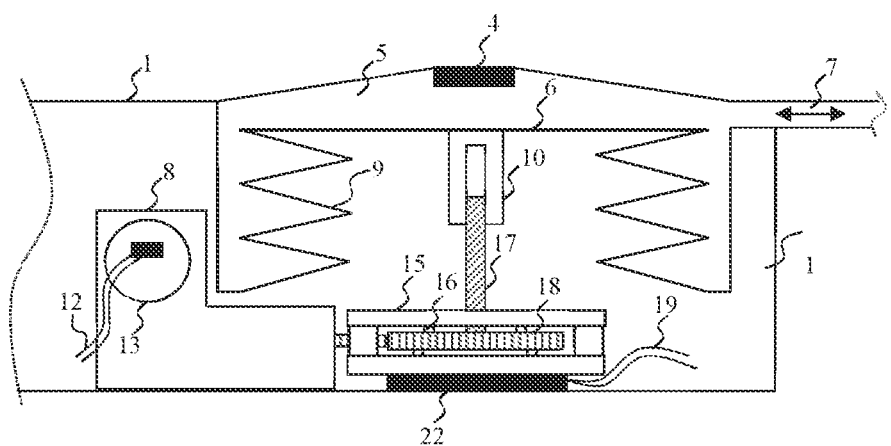

FIG. 3 illustrates another embodiment of the invention and represents a sectional view of a portion of the inside of the casing 1.

The elements bearing the same reference signs as in FIG. 2 fulfill the same function and will therefore not be described again.

In this embodiment, the force sensor 22 may for example be based on a measurement with strain gauge(s). The sensor 22 is attached on the block 15 and on the wall of the casing facing said block, on the opposite side to the reservoir. The force sensor 22 is able to measure both compressive and traction forces. The pre—stress device of the embodiment of FIG. 2 is not necessary in this case.

Figure 4:
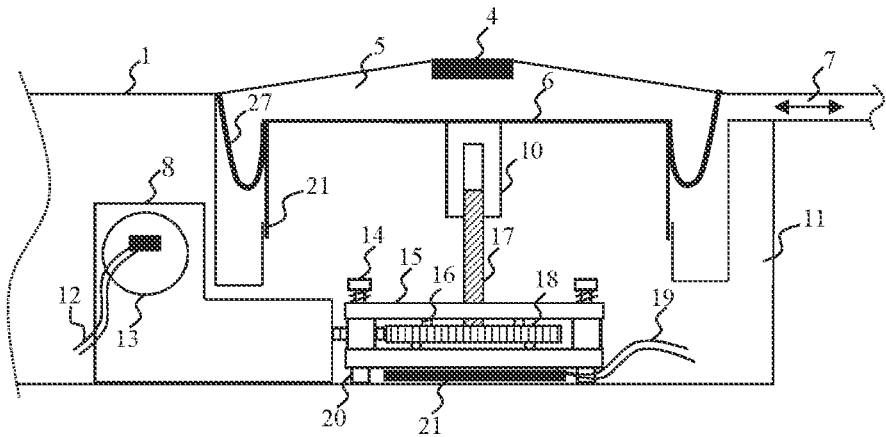

FIG. 4 illustrates an embodiment of the invention and represents a sectional view of a portion of the inside of the casing 1.

In this embodiment, the movable portion of the reservoir 5 is not bellows but a rolling membrane 27. As in FIG. 2, the force sensor 21 only measures compressive forces and is therefore associated with a pre—stress device 14.

Figure 5:
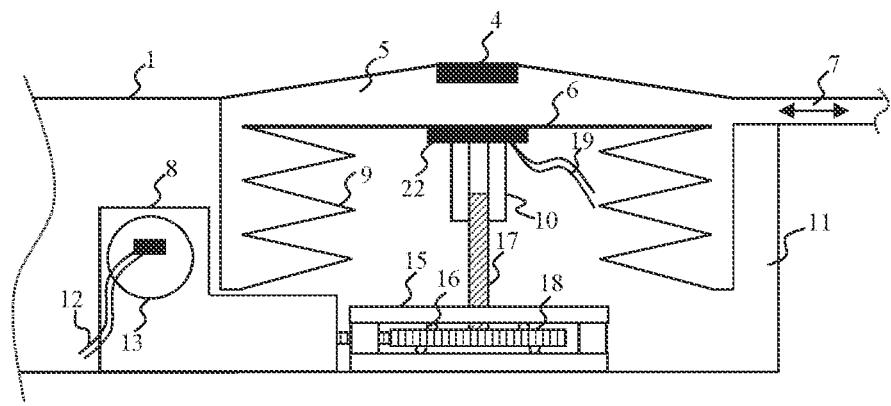

FIG. 5 illustrates another embodiment of the invention and represents a sectional view of a portion of the inside of the casing 1.

The elements bearing the same reference signs as in FIG. 2 fulfill the same function and will therefore not be described again.

In this embodiment, the force sensor 22 may for example be based on a measurement with strain gauge(s). It may be integrated between the tapped spotted wheel 10 and the flange 6. The tapped spotted wheel 10 and the force sensor 22 may also form a single and complete assembly integrating the strain gauge(s) and a tapped portion, thereby fulfilling the force measurement and of drive by the driving screw 17. The force sensor 22 is able to measure both compressive and traction forces. The pre—stress device of the embodiment of FIG. 2 is not necessary in this case.

Figure 10:
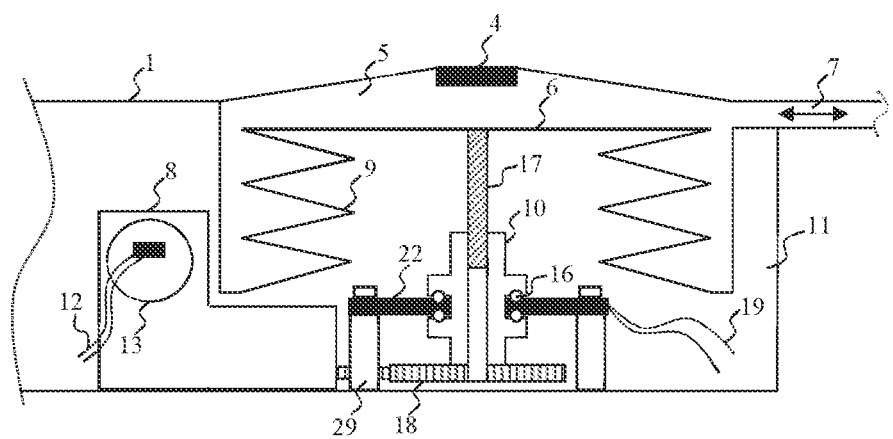
FIG. 10 is a sectional view of the casing of an implantable occlusive system according to a fifth embodiment of the invention.

FIG. 10 illustrates another embodiment of the invention and illustrates a sectional view of a portion of the inside of the casing 1.

The elements bearing the same reference signs as on FIG. 2 fulfill the same function and will therefore not be described again.

In this embodiment, the screw 17 is secured to the movable flange 6 of the bellows 9 and does not rotate. The linear movement of the flange 6 of bellows 9 is performed by means of the rotation of the nut 10 which linearly drives the screw 17. The nut 10 is secured to the wheel 18 which is driven by the reducer gear 8. The nut 10 is laid out so that only one rotation around the axis of the screw 17 is allowed. For this, a dual-effect bead abutment is laid out on the force sensor 22, by means of beads 16 which allow the nut 10 to turn and support the forces experienced along the axis of the screw 17. The forces exerted on the nut 10 are identical with the exerted ones in the other configurations.

Figure 11:
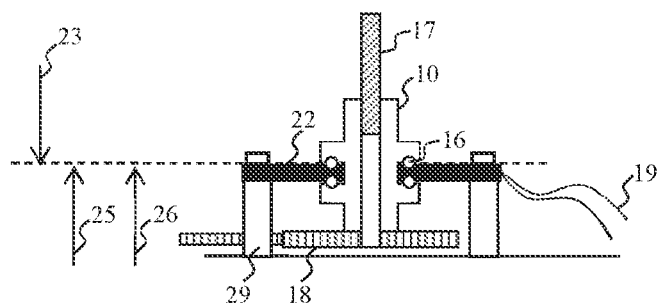
FIG. 11 is a sectional view of the force sensor and of the actuator of the system of FIG. 10, with an illustration of the measured forces.

FIG. 11 illustrates the main forces experienced and measured by the force sensor 22 with the purpose of inferring therefrom the pressure in the fluidic circuit. For measuring force in the two directions along the axis of the screw 17, the force sensor 22 is integrated into the bead abutment 16 so as to be able to measure forces in both directions. The supports 29 give the possibility of maintaining the force sensor 21. In this embodiment, the forces 23, and 26 are measured by the force sensor at the bead abutment 16 integrated into the driving nut 10. The force sensor may be in this case a sensor comprising strain gauges placed so as to measure forces in both directions along the axis of the screw 17 secured to the flange 6 of the bellows 9.

The embodiment illustrated in FIGS. 10 and 11 has the advantage of allowing a gain in space and gives the possibility of obtaining a larger travel of the bellows for the same dimensions of the implant, as compared with other embodiments. The mechanical integration is moreover simpler.

Determination of the Pressure in the Fluidic Circuit of the Occlusion System

The pressure in the fluidic circuit is determined indirectly. As this was indicated in the preamble, the integration of a pressure sensor on one of the walls of the reservoir of variable volume or on one of the portions of the fluidic circuit would be a restriction and would have several drawbacks.

Instead of such a sensor, the present invention uses the movable portion of the reservoir with variable volume for indirectly measuring the pressure in the fluidic circuit of the occlusive system.

The implantable system therefore comprises a device for measuring the fluid pressure in the fluidic circuit, which comprises said force sensor and a processing unit (for example a microprocessor) coupled with said sensor. The processing unit takes into account the force measurements acquired by said sensor, as well as other mechanical, physical and dimensional parameters of the system, for determining the fluid pressure in the fluidic circuit.

In order to measure a relative pressure in the fluidic circuit, a sensor (for example a barometric sensor) allowing measurement of the current atmospheric pressure may be laid out in an external device borne by the patient in order to take into consideration the changes of atmospheric pressure related to the altitude and/or weather conditions.

Another embodiment may be based on the measurement of the current atmospheric pressure directly from the fluidic circuit when one is sure under determined conditions of having a pressure in the fluidic circuit equal to a known relative pressure (for example, zero relative pressure for a particular position of the movable portion of the reservoir).

The measurement of the atmospheric pressure is then taken into account in both embodiments described below for inferring therefrom a relative pressure from a measurement of absolute pressure as described below.

The description below is based on a force sensor only measuring the compression (not traction). The same principle may be applied for force sensors measuring compressions and tractions. In this case, one does without the pre—stress system allowing generation of an "offset" on the force for measuring both compressive and traction forces.

Figure 6:
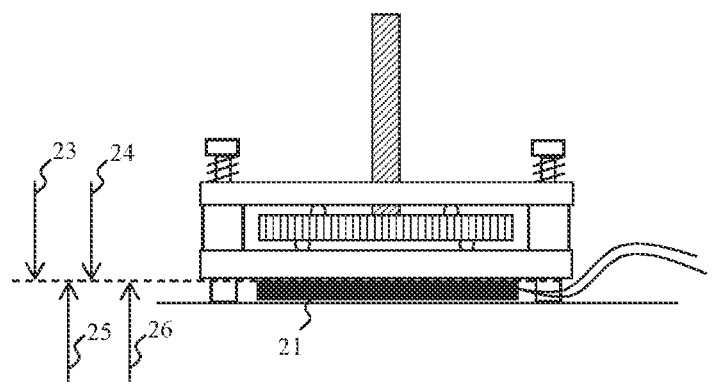

FIG. 6 illustrates the different forces measured by the force sensor, within the scope of the embodiment of FIG. 2:
the mark 23 refers to the force relatively to the pressure in the fluidic circuit;
the mark 24 refers to the pre—stress force;
the mark 25 refers to the force related to the stiffness of the bellows;
the mark 26 refers to the force related to the gas pressure in the casing.

Figure 7:
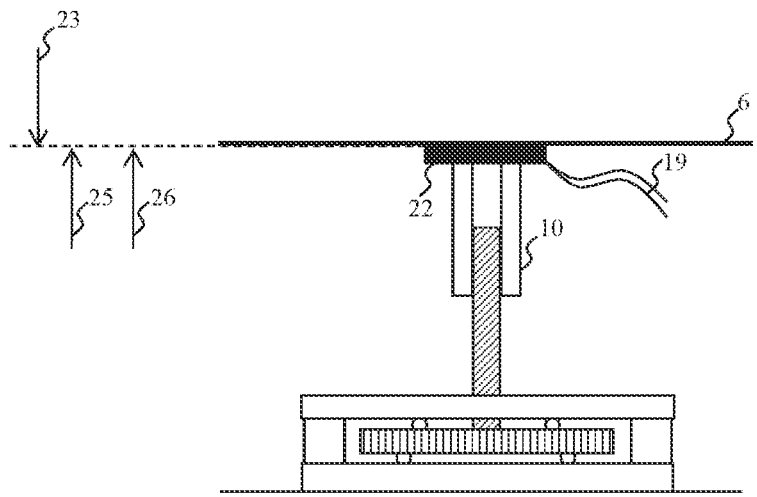

FIG. 7 illustrates the different forces measured by the force sensor placed at the tapped spotted wheel 10 and at the movable wall (flange 6), within the scope of the embodiment of FIG. 5:
the mark 23 refers to the force relative to the pressure in the fluidic circuit;
the mark 25 refers to the force related to the stiffness of the bellows;
the mark 26 refers to the force related to the gas pressure in the casing.

In order to infer the pressure P1 in the fluidic circuit, the considered parameters are the following:
$S_{eff}$: the effective pressure surface area of the movable portion of the reservoir with a variable volume (as indicated above, this surface area may be fixed or variable depending on the configuration of the system);
$F_{prest}$: the force generated by the pre—stress system;
K: the stiffness related to the reservoir with variable volume (case of bellows for example), the latter may be neglected in certain configurations of the reservoir of variable volume (the case of a system with a rolling membrane or a piston);
i: the relative position of the movable portion of the reservoir with a variable volume relatively to a reference position,
$F_{losses}$: the mechanical losses related to friction of the different mechanical parts during transmission of the forces on the force sensor.
$F_{sensor}$: the force measured by the force sensor(s).
$P_{casing}$: the pressure of the gas contained in the implantable hermetic casing, said pressure may either be inferred from the position of the movable portion relatively to its reference position and from the effective pressure surface area of the movable portion, or be measured by a gas pressure sensor placed in the casing (optional).

From these elements, several forces applied on the movable wall of the reservoir with a variable volume may be inferred therefrom:
$F_{occl}$: the (positive or negative) force reduced on the movable portion of the reservoir of variable volume related to the pressure in the fluidic circuit of the occlusion system;
$F_{casing}$: the (positive or negative) force reduced on the movable portion of the reservoir of variable volume related to the pressure in the implantable hermetic casing;
$F_{wall}$: the force related to the position and to the stiffness of the movable portion of the reservoir of variable volume.

Subsequently it is considered that the gas pressure in the casing is inferred from the position of the movable portion relatively to its reference position and from the effective pressure surface area of the movable portion.

The balance of the forces on the force sensor is expressed in the following way:

$$F_{sensor} = F_{occl} + F_{prest} - F_{wall} - F_{casing} - F_{losses}$$

with:

$$F_{occl} = P \cdot S_{eff}$$

$$F_{wall} = K \cdot i$$

$$F_{casing} = P_{init} \cdot \left( \frac{V_{init}}{V_{init} - S_{eff} \cdot i} - 1 \right) \cdot S_{eff}$$

with $P_{init}$ and $V_{init}$ being constants corresponding to the initial pressure and the initial gas volume respectively in the casing when the latter has been hermetically sealed.

$P_{init}$ may for example be equal to atmospheric pressure when the casing is hermetically sealed.

The force generated by the pre—stress device allows generation of an "offset" on the force sensor which allows measurement of positive and negative forces.

The $F_{casing}$ force is inferred from the position of the movable wall relatively to its origin and from the effective pressure surface area of the movable wall. In this case it is considered that the casing is perfectly hermetic. It is also possible to assume a negligible loss of gas of the casing outwards which may either be neglected or taken into account in the calculation of the force $F_{casing}$. Finally, the force $F_{casing}$ may also be directly measured by a pressure sensor and inferred by multiplying by the surface $S_{eff}$.

The pressure P1 of the fluidic circuit of the occlusion system may therefore be inferred therefrom:

$$P1 = \frac{F_{sensor} - F_{prest} + F_{wall} + F_{casing} + F_{losses}}{S_{eff}}$$

$$P1 = \frac{F_{sensor} - F_{prest} + K \cdot i + F_{losses}}{S_{eff}} + P_{init} \cdot \left( \frac{V_{init}}{V_{init} - S_{eff} \cdot i} - 1 \right)$$

with $F_{prest}$ and $F_{losses}$ being known constants.

The force $F_{prest}$ may be generated by pre—stressed springs. As the displacement of the block 15 is very small, it may considered that the travel of the springs may be neglected relatively to their stiffness and that the pre—stress force is constant.

$F_{prest}$ is selected so as to be able to measure negative and positive pressures over the whole desired measurement range.

In the case when the force sensor is capable of measuring compressive and traction forces, it is possible to remove the pre—stress system (case of the embodiments described in FIG. 3 and FIG. 5). In this case, the constant $F_{preset}$ considered in the calculations of P1.

In order to infer the relative pressure P2 in the fluidic circuit, the current atmospheric pressure exerted on the body of the patient should be taken into account. The measurement of the pressure Patm may be achieved as described in the previous paragraphs.

In this case, P2 is calculated in the following way:

$$P2=P1+(Pinit-Patm)$$

In a preferred embodiment, the casing is sealed so as to maximize the air volume in the casing (movable portion of the reservoir in an initial position so as to have a minimum volume in the reservoir of variable volume). This gives the possibility of having a pressure of the gas in the casing always positive regardless of the position of the movable wall.

The paragraphs below show two examples of measurement of the pressure from the method described in the present invention.

The device described in both examples below has the following characteristics:

$S_{eff}=1\times10^{-3}$ m$^2$
$K=5$ N/mm
$F_{prest}=20$ N
$V_{init}=10\times10^{-5}$ m$^3$
$P_{init}=1{,}000$ hPa
$P_{atm}=900$ hPa
$F_{losses}=0$ N We have considered in these examples that the atmospheric pressure during the sealing of the casing (Pinit) is different from the atmospheric pressure (Patm) exerted on the body of the patient during the measurement of the pressure in the fluidic circuit.

Example 1: measurement of the pressure in the fluidic circuit from a device according to the embodiment described in FIG. 2, comprising a force sensor only measuring compressive forces.

For i=0 (upper position of the bellows, corresponding to a minimum volume of the reservoir), the processing unit performs the following calculation for measuring the pressure P1 in the fluidic circuit:

$$P1 = \frac{F_{sensor} - 20}{1 \times 10^{-3}}$$

For a relative zero pressure in the fluidic circuit for example, the force sensor measures the compressive force of the pre—stress (20 N), as well as the force related to the atmospheric pressure difference (900 hPa) exerted on the body of the patient and therefore on the flexible occlusive sleeve and the gas pressure in the casing (1,000 hPa) i.e. a value P1 calculated by the processing unit:

$$F\,sensor = 20N + S_{eff} \times (Patm - Pinit)$$

$$F\,sensor = 20N + 1.10^{-3} \times (90000 - 100000) = 10N$$

$$P1 = \frac{10-20}{1\times 10^{-3}} = -10 \text{ kPa}$$

The relative pressure P2 in the fluidic circuit may be inferred therefrom:

$$P2=P1+(Pinit-Patm)$$

$$P2=-10000+(100000-90000)=0 Pa$$

For a relative pressure in the fluidic circuit of 5 kPa for example, the force on the force sensor is the one generated by the pressure in the fluidic circuit $F_{occl}$ (i.e. 5 N), that of the pre—stress (i.e. 20 N), and that related to the atmospheric pressure (−10 N) or a resulting force of 15 N, or a value calculated by the processing unit:

$$P1 = \frac{15-20}{1\times 10^{-3}} = -5 \text{ kPa}$$

The relative pressure P2 in the fluidic circuit may be inferred therefrom:

$$P2=P1+(Pinit-Patm)$$

$$P2=-5000+(100000-90000)=5 \text{ kPa}$$

For a relative pressure in the fluidic circuit of −5 kPa for example, the force on the force sensor is the one generated by the pressure in the fluidic circuit $F_{occl}$ (i.e. −5 N), that of the pre—stress (i.e. 20 N), and that related to the atmospheric pressure (i.e. −10 N) i.e. a resulting force of 5 N, i.e. a value calculated by the processing unit:

$$P1 = \frac{5-20}{1\times 10^{-3}} = -15 \text{ kPa}$$

The relative pressure P2 in the fluidic circuit may be inferred therefrom:

$$P2=P1+(Pinit-Patm)$$

$$P2=-15000+(100000-90000)=-5 \text{ kPa}$$

For i=4 mm for example (low position of the bellows, generating a gas compression in the casing and a return force related to the stiffness of the bellows), the processing unit performs the following calculation for measuring the pressure in the fluidic circuit:

$$P1 = \frac{F\,sensor - 5\times 4 + 20}{1\times 10^{-3}} + 100000 \times \left(\frac{10\cdot 10^{-5}}{10\cdot 10^{-5} - 1\cdot 10^{-3}\times 4\cdot 10^{-3}} - 1\right)$$

$$P1 = \frac{F\,sensor}{1\times 10^{-3}} + 100000 \times \left(\frac{10\cdot 10^{-5}}{10\cdot 10^{-5} - 1\cdot 10^{-3}\times 4\cdot 10^{-3}} - 1\right)$$

$$P1 = \frac{F\,sensor}{1\times 10^{-3}} + 4166{,}67$$

For zero relative pressure in the fluidic circuit for example, the forces on the force sensor are $F_{prest}$ (20 N), $F_{wall}$ (−20 N), $F_{casing}$ (−4.167 N) and the force related to the atmospheric pressure (i.e. −10 N) i.e. a resulting force of −14.167 N, i.e. a value calculated by the processing unit:

$$P1 = \frac{-14{,}167}{1\times 10^{-3}} + 4166{,}67 = -10 \text{ kPa}$$

The relative pressure P2 in the fluidic circuit may be inferred therefrom:

$$P2=P1+(Pinit-Patm)$$

$$P2=-10000+(100000-90000)=0 Pa$$

For a relative pressure in the fluidic circuit of 5 kPa for example, the forces on the force sensor are $F_{occl}$ (5 N), $F_{prest}$ (20 N), $F_{wall}$ (−20 N), $F_{casing}$ (−4.167 N) and the force related to the atmospheric pressure (i.e. −10 N) i.e. a resulting force of −9.167 N i.e. a value calculated by the processing unit:

$$P1 = \frac{-9{,}167}{1 \times 10^{-3}} + 4166{,}67 = -5 \, kPa$$

The relative pressure P2 in the fluidic circuit may be inferred therefrom:

$$P2=P1+(Pinit-Patm)$$

$$P2=-5000+(100000-90000)=5 \text{ kPa}$$

For a relative pressure in the fluidic circuit of −5 kPa for example, the forces on the force sensor are $F_{occl}$ (−5 N), $F_{prest}$ (20 N), $F_{wall}$ (−20 N), $F_{casing}$ (−4.167 N) and the force related to the atmospheric pressure (i.e. −10 N) i.e. a resulting force of −19.167 N, i.e. a value calculated by the processing unit:

$$P1 = \frac{-19{,}167}{1 \times 10^{-3}} + 4166{,}67 = -15 \, kPa$$

The relative pressure P2 in the fluidic circuit may be inferred therefrom:

$$P2=P1+(Pinit-Patm)$$

$$P2=-15000+(100000-90000)=-5 \text{ kPa}$$

Example 2: measurement of the pressure in the fluidic circuit from a device based on the embodiment described in FIG. 5, comprising a force sensor capable of measuring compressive forces and traction forces.

For i=0, the processing unit performs the following calculation for measuring the pressure in the fluidic circuit:

$$P1 = \frac{F \, \text{sensor}}{1 \times 10^{-3}}$$

For a zero relative pressure in the fluidic circuit for example, the force sensor only measures a force related to the atmospheric pressure difference (900 hPa) exerted on the body of the patient, and therefore on the flexible occlusive sleeve, and the gas pressure in the casing (1,000 hPa) corresponding to a force of −10 N, i.e. a value calculated by the processing unit:

$$P1 = \frac{-10}{1 \times 10^{-3}} = -10 \, kPa$$

The relative pressure P2 in the fluidic circuit may be inferred therefrom:

$$P2=P1+(Pinit-Patm)$$

$$P2=-10000+(100000-90000)=0 Pa$$

For a relative pressure in the fluidic circuit of 5 kPa for example, the only force on the force sensor is the one generated by the pressure in the fluidic circuit $F_{occl}$ (i.e. 5 N), and the force related to the atmospheric pressure (i.e. −10 N) i.e. a value calculated by the processing unit:

$$P1 = \frac{-5}{1 \times 10^{-3}} = -5 \, kPa$$

The relative pressure P2 in the fluidic circuit may be inferred therefrom:

$$P2=P1+(Pinit-Patm)$$

$$P2=-5000+(100000-90000)=5 \text{ kPa}$$

For a relative pressure in the fluidic circuit of −5 kPa for example, the only force on the force sensor is the one generated by the pressure in the fluidic circuit $F_{occl}$ (i.e. −5 N), and the force related to the atmospheric pressure (i.e. −10 N) i.e. a value calculated by the processing unit:

$$P1 = \frac{-15}{1 \times 10^{-3}} = -15 \, kPa$$

The relative pressure P2 in the fluidic circuit may be inferred therefrom:

$$P2=P1+(Pinit-Patm)$$

$$P2=-15000+(100000-90000)=-5 \text{ kPa}$$

For i=4 mm, the processing unit performs the following calculation for measuring the pressure in the fluidic circuit.

$$P1 = \frac{F \, \text{sensor} + 5 \times 4}{1 \times 10^{-3}} + 100000 \times \left( \frac{10 \cdot 10^{-5}}{10 \cdot 10^{-5} - 1 \cdot 10^{-3} \times 4 \cdot 10^{-3}} - 1 \right)$$

$$P1 = \frac{F \, \text{sensor} + 20}{1 \times 10^{-3}} + 4166{,}67$$

For zero relative pressure in the fluidic circuit for example, the forces on the force sensor are $F_{wall}$ (−20 N) and $F_{casing}$ (−4.167 N) and the force related to the atmospheric pressure (i.e. −10 N) i.e. a resulting force of −34.167 N, i.e. a value calculated by the processing unit:

$$P1 = \frac{-34{,}167 + 20}{1 \times 10^{-3}} + 4166{,}67 = -10 \, kPa$$

The relative pressure P2 in the fluidic circuit may be inferred therefrom:

$$P2=P1+(Pinit-Patm)$$

$$P2=-10000+(100000-90000)=0 Pa$$

For a relative pressure in the fluidic circuit of 5 kPa for example, the forces on the force sensor are $F_{occl}$ (5 N), $F_{wall}$ (−20 N) and $F_{casing}$ (−4.167 N), and the force related to the atmospheric pressure (i.e. −10 N) i.e. a resulting force of −29.167 N, i.e. a value calculated by the processing unit:

$$P1 = \frac{-29{,}167 + 20}{1 \times 10^{-3}} + 4166{,}67 = -5 \, kPa$$

The relative pressure P2 in the fluidic circuit may be inferred therefrom:

$$P2 = P1 + (Pinit - Patm)$$

$$P2 = -5000 + (100000 - 90000) = 5 \text{ kPa}$$

For a relative pressure in the fluidic circuit of −5 kPa for example, the forces on the force sensor are $F_{occl}$ (−5 N), $F_{wall}$ (−20 N) and $F_{casing}$ (−4.167 N), and the force related to the atmospheric pressure (i.e. −10 N) i.e. a resulting force of −39.167 N, i.e. a value calculated by the processing unit:

$$P1 = \frac{-39{,}167 + 20}{1 \times 10^{-3}} + 4166{,}67 = -15 \text{ k Pa}$$

The relative pressure P2 in the fluidic circuit may be inferred therefrom:

$$P2 = P1 + (Pinit - Patm)$$

$$P2 = -15000 + (100000 - 90000) = -5 \text{ kPa}$$

In both examples above, it is assumed that the device does not comprise any pressure sensor measuring the pressure of gas in the casing.

In a configuration where the device comprises a pressure sensor measuring the gas pressure in the casing, it is sufficient to replace the term $$F_{casing} = P_{init} \cdot \left( \frac{V_{init}}{V_{init} - S_{eff} \cdot i} - 1 \right) \cdot S_{eff} \text{ with } P \text{ sensor}$$

with Psensor being the measurement value of the gas pressure sensor.

It should be noted that the present invention may also be applied to devices including a reservoir with variable volume without any mechanical stiffness of the piston or rolling membrane type. In this case, the stiffness K in the calculation of the pressure P is considered as zero or negligible.

Pressure Control of the Occlusive System

As the preferred goal of the system is to control the pressure, a closed loop regulation of the pressure first seems to be the wisest choice for the pressurization of the occlusion system. However, the pressure in the occlusion system is not only dependent on the pressurization system. Outer effects related to the movements of the organs of the patient or to his/her breathing for example may generate pressures which will be measured by the pressure measurement system described earlier.

This may have the effect, during the pressure server control, of inducing excessive stressing of the actuator and therefore a too large electric consumption. Indeed, the outer pressures may vary during a change in the pressure of the occlusion system, the server control system will tend to try and compensate for these variations, which will generate excessive stressing of the actuator.

In order to find a remedy to this problem, one of the objects of this invention is to propose a simple method for controlling pressure of the pressurization system. Rather than subordinate the system as regards pressure, the actuator is controlled by position server control of the movable portion of the reservoir with variable volume. Knowing the effective pressure surface area of the movable portion at each position, this therefore corresponds to a volume server control of the occlusion system.

Tests conducted in vitro and in vivo ([1]) have shown that the relationship between the pressure in the fluidic circuit and the volume injected into the occlusion system have a defined and repeatable relationship over time. This is true under particular conditions of the patient, i.e. when the latter is motionless and in a determined position (stretched out or standing for example).

The device for controlling the fluid pressure in the fluidic circuit notably comprises a memory in which is recorded a relationship between the pressure in the fluidic circuit and the volume injected from or to the reservoir, a processing unit (optionally identical with the processing unit of the device for measuring the pressure in the fluidic circuit) and a calibration unit, the operation of which is described hereafter.

Figure 8:
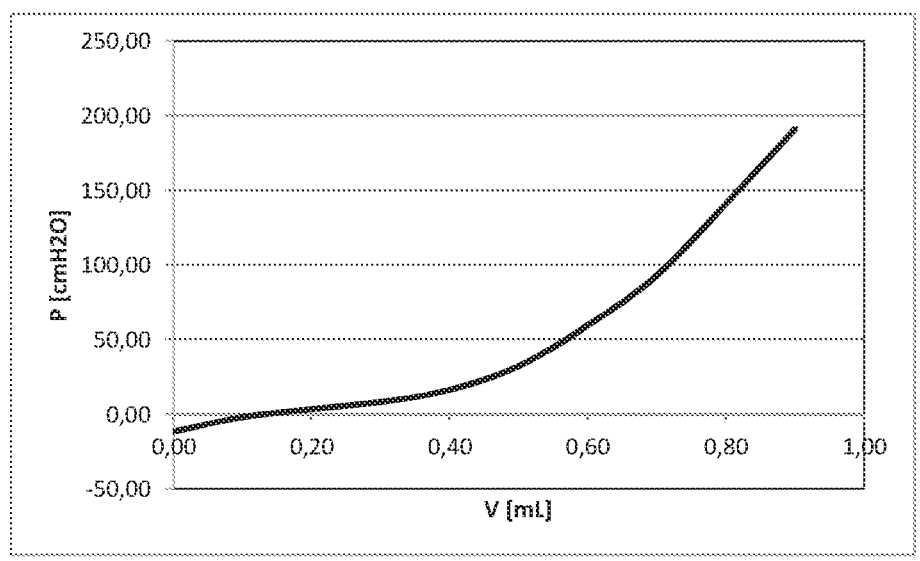

FIG. 8 is a graph illustrating the variation of the pressure in the fluidic circuit versus the volume injected into the fluidic circuit from the reservoir. It should be noted that the pressure relationship depending on the injected or removed volume may have hysteresis, i.e. the pressure curve during a rise in pressure may be different from the pressure curve during a drop in pressure. In order to be able to control the system as regards pressure, the pressurization system regularly conducts pressure measurements for given injection volumes. This calibration procedure is carried out under predetermined conditions. For example in the case of an artificial urinary sphincter, the calibration may be achieved a few minutes after urination and when the patient is standing and substantially motionless. For this purpose, the pressurization system gradually increases the pressure for predetermined injection volumes and records the measured values in a table localized in the memory of the implant. This calibration procedure may be carried out at a defined time period, for example every week, or else upon an examination by a physician, by means of a programmer in wireless communication with the implant. In every case, the current atmospheric pressure should be able to be recovered for carrying out an accurate pressure measurement in the fluidic circuit regardless of the altitude or of the weather conditions of the location where the patient is found during the calibration.

Figure 9:
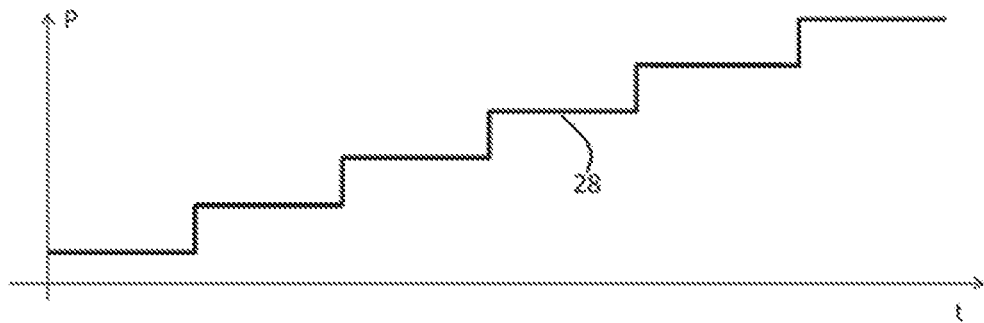

FIG. 9 is a graph illustrating the variation 28 of the pressure P2 in the fluidic circuit versus time t for different fluid volumes injected into the occlusive sleeve during the calibration procedure.

The calibration may be carried out additionally when the patient is in a stretched—out position and substantially motionless. This gives the possibility of recording pressure values which will be different from those recorded when the patient is standing, because of the water column between the implantable casing and the occlusive sleeve implanted at different heights in the patient.

The calibration may take into account the hysteresis which may exist in the fluidic circuit. In this case, the memory of the implant includes a table containing the values of the volume to be injected in order to attain a given pressure as well the values of the volume to be withdrawn in order to attain a given pressure.

During normal operation, when a command for pressurization at a given pressure is sent to the pressurization system, the volume corresponding to the set pressure value is looked up in the table in memory and is used for pressurizing the occlusion system to the desired pressure.

As a safety step, the pressure may be measured during the pressurization phase in order to ensure proper operation of the device and a match with the expected pressure values.

In order to measure the movement of the patient and determine whether he/she is motionless, and for measuring his/her posture and determine whether he/she is standing or stretched out, an accelerometer may be used.

In order to achieve the procedure for calibrating the volume versus the pressure in the occlusion system, a clock is used. For example it may be of the RTC type.

Safety System

In the case when the pressure in the fluidic circuit becomes very high and close to the limits defined in the technical recommendations relating to the pressure strength of the different elements of the fluidic circuit, the processing unit may automatically send an order for decompressing the occlusive sleeve.

According to a particularly advantageous embodiment of the invention, the device for actuating the sleeve comprises a member for reducing the mechanical stresses caused by too large pressure in the fluidic circuit, giving the possibility of protecting the actuation device from risks of deterioration.

The mechanical stresses experienced by the actuation device resulting from too large pressure in the fluidic circuit may become very significant, which may cause deterioration of one or more of the portions of the actuation device. The pressurization system, the tubing, the sleeve, the pressure sensor and/or the connectors may be concerned by this degradation.

In order to avoid deterioration of the actuation device, the stress—reducing member is designed for, when the mechanical stresses (pressure in the fluidic circuit) exceed a determined stress threshold, absorbing a portion of said stresses so as to reduce the stresses experienced by the actuation device.

The stress—reducing member is dimensioned so as to reduce the stresses down to a level at which they are too low for a risk of damaging the actuation device while being sufficiently high so as to not totally release the compression exerted by the sleeve.

Depending on the contemplated method for reducing stresses and on the structure of the actuation device, the person skilled in the art is able to design a member fulfilling these conditions.

According to an embodiment, the stress—reducing member comprises an expansion chamber laid out in the hydraulic circuit and being mechanically triggered when the pressure in the fluidic circuit exceeds a defined threshold. This has the effect of transferring a portion of the fluid of the hydraulic circuit towards the expansion chamber in order to reduce the pressure in the latter.

Alternatively, the stress—reducing member may comprise a piston coupled with a spring system having a sufficiently high stiffness for remaining substantially fixed when the pressure in the hydraulic circuit corresponds to the normal operating pressure of the device and movable under the effect of a higher pressure.

The stress—reducing member may have different embodiments; for example and in a non—limiting way:

- a valve coupled with a spring or a specific material in an expansion chamber;
- a component of the hydraulic circuit made of a flexible material having the property of deforming from a certain pressure threshold;
- a deformable membrane beyond a certain pressure threshold or depending on the applied pressure;
- the reservoir with variable volume designed so as to be deformable beyond a certain pressure threshold or depending on the applied pressure;
- the actuation mechanism designed so as to be deformable beyond a certain pressure threshold or depending on the applied pressure.

REFERENCES

EP 1 584 303
U.S. Pat. No. 8,585,580
U.S. Pat. No. 4,581,018
U.S. Pat. No. 4,222,377
CA 1,248,303
U.S. Pat. No. 4,408,597
[1] Lamraoui, H; Bonvilain, A; Robain, G; Combrisson, H; Basrour, S; Moreau—Gaudry, A; Cinquin, P; Mozer, P "Development of a Novel Artificial Urinary Sphincter: A Versatile Automated Device", IEEE—ASME Transactions on Mechatronics, 15, 916–924, 2010.

The invention claimed is:

1. An occlusion system implantable in a human or animal body, comprising:
   a casing made of a biocompatible material;
   an inflatable occlusive sleeve outside the casing, the inflatable occlusive sleeve being configured to surround an anatomical duct;
   a reservoir filled with a fluid arranged within the casing, the reservoir comprising a fixed portion and a movable portion defining together a fluid volume of the reservoir;
   a tubing fluidically coupling the reservoir to the inflatable occlusive sleeve;
   an actuator mechanically coupled with the movable portion of the reservoir and configured to displace said movable portion relative to the fixed portion for adjusting the fluid volume of the reservoir, wherein the fluid volume adjustment moves fluid between the reservoir and the occlusive sleeve through the tubing;
   a control unit configured to command the actuator based on a pressure to be applied by the occlusive sleeve onto the anatomical duct; and
   at least one force sensor comprising one or several strain gauges in a mechanical connection with at least one of the actuator and the movable wall of the reservoir to measure a compressive and a traction force in a direction of displacement of the movable wall.

2. The occlusion system of claim 1, wherein the movable portion of the reservoir comprises a movable wall and bellows extending from the movable wall, the wall being coupled to a drive system configured to linearly move the wall, the linear movement of the wall compressing or expanding the bellows.

3. The occlusion system of claim 2, wherein the drive system comprises a screw secured to the movable wall and a nut coupled with the screw, the nut being movable in rotation around an axis of the screw under the effect of a driving action by the actuator, the nut being coupled with the screw in a manner that a rotation of the nut drives the screw only in translational motion.

4. The occlusion system of claim 1, further comprising an accelerometer, the control unit being configured for, from measurement data of the accelerometer, determining whether the body is in a determined situation.

5. The occlusion system of claim 1, wherein the actuator is selected from piezoelectric actuators, electromagnetic actuators, electro—active polymers and shape memory alloys.

6. The occlusion system of claim 1, wherein the actuator is electrically connected to a power source within the casing.

7. The system occlusive according to claim 1, wherein the casing is hermetically sealed and comprises a gas pressure sensor for measuring a gas pressure in the casing.

8. The occlusive system of claim 1, further comprising an external device configured to be held by the patient, and configured to communicate wirelessly with the control unit.

* * * * *